United States Patent
Polonka

(10) Patent No.: US 8,524,203 B2
(45) Date of Patent: Sep. 3, 2013

(54) SUNSCREEN COMPOSITE PARTICLES FOR UVA AND UVB PROTECTION

(75) Inventor: Jack Polonka, Peekskill, NY (US)

(73) Assignee: Conopco, Inc., Englewood Cliffs, NJ (US)

( * ) Notice: Subject to any disclaimer, the term of this patent is extended or adjusted under 35 U.S.C. 154(b) by 179 days.

(21) Appl. No.: 12/888,896

(22) Filed: Sep. 23, 2010

(65) Prior Publication Data

US 2012/0076741 A1  Mar. 29, 2012

(51) Int. Cl.
  *A61K 8/00* (2006.01)
  *A61K 8/18* (2006.01)
  *A61K 9/00* (2006.01)
  *A61K 8/02* (2006.01)
  *A61Q 17/04* (2006.01)

(52) U.S. Cl.
  USPC ............................. 424/59; 424/400; 424/401

(58) Field of Classification Search
  USPC ............................................ 424/59, 400, 401
  See application file for complete search history.

(56) References Cited

U.S. PATENT DOCUMENTS

| | | | |
|---|---|---|---|
| 4,387,089 A | 6/1983 | De Polo | |
| 6,306,373 B1 | 10/2001 | Impernate et al. | |
| 6,485,713 B1 | 11/2002 | Bonda et al. | |
| 6,492,458 B1 | 12/2002 | Pavlin | |
| 7,329,719 B2 | 2/2008 | Pavlin | |
| 7,476,395 B2 | 1/2009 | Polonka et al. | |
| 2007/0297997 A1* | 12/2007 | Tanner | 424/59 |
| 2009/0324659 A1* | 12/2009 | Polonka et al. | 424/401 |
| 2011/0104082 A1* | 5/2011 | Polonka et al. | 424/59 |

OTHER PUBLICATIONS

PCT International Search Report and Written Opinion on International Appl. No. PCT/EP2011/063599 dated Jan. 22, 2013.

* cited by examiner

*Primary Examiner* — Mina Haghighatian
*Assistant Examiner* — Luke Karpinski
(74) *Attorney, Agent, or Firm* — Edward A. Squillante, Jr.

(57) ABSTRACT

Sunscreen composite particles for UVA and UVB protection are described. The particles are substantially free of supplied UVB sunscreen and are prepared with a UVA sunscreen suitable to undergo keto-enol tautomerization.

3 Claims, No Drawings

SUNSCREEN COMPOSITE PARTICLES FOR UVA AND UVB PROTECTION

FIELD OF THE INVENTION

The present invention is directed to obtaining UVA and UVB protection from a traditional UVA sunscreen. More particularly, the present invention is directed to sunscreen composite particles suitable for use in compositions displaying both UVA and UVB protection. The compositions comprising such sunscreen composite particles surprisingly provide for both improved UVA protection, and UVB protection, notwithstanding the fact that the particles comprise a traditional UVA sunscreen and are substantially free of supplied UVB sunscreen.

BACKGROUND OF THE INVENTION

Ultraviolet radiation can be damaging to skin. Immediate damage may be in the form of erythma. More long term is the concern of carcinomas or even melanoma. For these reasons, photoprotective agents, known as sunscreens, have been incorporated into cosmetic compositions.

It is known, generally, that the sun's UVA radiation has wavelengths between 320 and 400 nm. Such UVA radiation can burn the skin and overexposure has been linked to skin cancer. The sun's UVB radiation has a wavelength between 280 and 320 nm and has also been linked to short and long-term skin damage including deep wrinkle formation, collagen breakdown and mottled pigmentation. Protection from the sun's UVA and UVB rays is, therefore, desired.

Dibenzoylmethane derivatives are known sunscreens capable of absorbing UVA rays. While often used, these sunscreens are relatively sensitive to UV rays and tend to decompose upon exposure to sunlight. Moreover, dibenzoylmethane derivatives, which are essentially ineffective as a UVB radiation protector, are often formulated with UVB radiation sunscreens like p-methoxycinnamic acid. Unfortunately, UVB radiation sunscreens tend to accelerate the photodecomposition of dibenzoylmethane derivatives. Thus, compositions with both dibenzoylmethane derivatives and p-methoxycinnamic acid need to be applied frequently by consumers in order to ensure adequate protection from the sun's rays.

There is a need to generate topical sunscreen compositions that provide both UVA and UVB protection and that do not rapidly lose their benefit in the presence of sunlight. Moreover, there is a need to generate topical sunscreen compositions where the UVA and/or UVB sunscreens do not interfere with additional ingredients in the compositions, including each other.

This invention, therefore, is directed to sunscreen composite particles and compositions comprising the same. The particles comprise a traditional UVA sunscreen, are unexpectedly suitable to provide both improved UVA protection, and UVB protection and are substantially free of supplied UVB sunscreen. Such particles may be used to formulate compositions that do not display rapid degradation of UVA sunscreen.

Additional Information

Efforts have been disclosed for making sunscreen compositions. In U.S. Pat. No. 4,387,089, light-screen compositions with 4-(1,1-dimethylethyl) 4'-methoxydibenzoylmethane are described.

Other efforts have been disclosed for making sunscreen compositions. In U.S. Pat. No. 6,306,373, a specific eutectic mixture using lower alkyl phthalimide in a sunscreen composition is described.

Still other efforts have been disclosed for making sunscreen compositions. In U.S. Patent Application Publication No. 2009/0324659, sunscreen composite particles for use in compositions are described.

None of the additional information above describes a sunscreen composite particle suitable for use in a composition displaying both UVA and UVB protection as claimed in this invention.

SUMMARY OF THE INVENTION

In a first aspect, the present invention is directed to a sunscreen composite particle comprising:
a) an UVA sunscreen suitable to undergo keto-enol tautomerization;
b) a resin; and
c) a solvent, the solvent being one in which the UVA sunscreen is soluble in and one having a dielectric constant from about 5.5 to about 9 wherein the particle imparts UVA and UVB sunscreen protection and is substantially free of supplied UVB sunscreen.

In a second aspect, the present invention is directed to a composition comprising the sunscreen composite particle of the first aspect of this invention.

In a third aspect, the present invention is directed to a method of providing UVA and UVB protection with the composition of the second aspect of this invention.

All other aspects of the present invention will more readily become apparent upon considering the detailed description and examples which follow.

Skin, as used herein, is meant to include skin on the face, neck, chest, back, arms, hands, legs, buttocks and scalp. Composition is meant to include the end use composition applied topically by consumers to skin. Substantially free of supplied UVB sunscreen means less than 5% by weight, and preferably, less than 1.5% by weight UVB sunscreen added to the particle, and most preferably, no UVB sunscreen supplied as an additive to the particle, all being based on total weight of the particle. Improved UVA protection means often about 1.5 times more UVA protection when compared to conventional compositions for UVA protection, the same being made without the sunscreen composite particles of this invention. Dielectric constant is measured according to the ASTM Procedure ISO/IEC 60250. Comprising, as used herein, is meant to include consisting essentially of and consisting of: Therefore, with respect to total weight of sunscreens, the particle of this invention can consist essentially of or consist of the UVA sunscreen defined herein. All ranges indentified herein are meant to include all ranges subsumed therein if reference to the same is not explicitly made.

DETAILED DESCRIPTION OF THE PREFERRED EMBODIMENTS

The only limitations with respect to the UVA sunscreen which may be used in this invention is that the same can undergo keto-enol tautomerization and is soluble in the solvent, where soluble is defined to mean the UVA sunscreen can dissolve in the solvent to yield a solution which is at least about 15%, and preferably, from about 25 to about 50%, and most preferably, from about 30 to about 45% by weight UVA sunscreen (based on total weight of UVA sunscreen and solvent), at about room temperature and including all ranges subsumed therein. The UVA sunscreens suitable for use in this invention include dibenzoylmethane and its derivatives. Preferred derivatives typically have the formula:

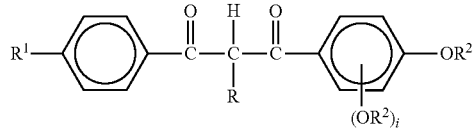

where
R is H or a $C_{1-3}$ alkyl;
$R^1$ is a linear or branched $C_{1-6}$ alkyl; and
each $R^2$ is independently a $C_{1-4}$ alkyl and i is zero or 1.

In a most preferred embodiment, R is hydrogen, $R^1$ is tert-butyl, $R^2$ is a methyl group, i is zero and the most preferred UVA sunscreen is 4-(1,1-dimethylethyl)-4'-methoxy-dibenzoylmethane (Avobenzone).

Composite particles of the present invention are formed with UVA sunscreen in solvent and a resin which is preferably condensation polymerizable. The condensation polymerizable resins suitable for use in this invention typically are characterized by an acid number ranging from about 3 to about 15 and a dielectric constant ranging from about 6.5 to about 18, including all ranges subsumed therein. The resin may be a polyester or polyamide and preferably comprises carboxylic acid groups. Most preferably chosen is the polyamide. Ester-terminated polyamides are especially desirable. Two examples are polyalkyleneoxypolyamide (PAOPA) and ester-terminated poly(ester-amide) (ETPEA) resins.

The polyalkyleneoxypolyamide resins that may be useful for making the sunscreen composite particle of this invention are outlined in U.S. Pat. No. 6,492,458 B1, the disclosure of which is incorporated herein by reference. These PAOPA materials may be prepared by combining reactants comprising a monocarboxylic acid compound, a diamine compound, and a dibasic acid. Specifics of these reactants are described herein below. Commercially the resins are available from the Arizona Chemical Company under the trademark Sylvaclear® PA 1200V, designated by INCI nomenclature as Polyamide-3, and as Sylvaclear® AF1900V. Exemplary monocarboxylic acids of the formula $R^1$—COOH include, without limitation, stearic acid ($C_{18}$), 1-eicosanoic acid ($C_{20}$), 1-docasanoic acid ($C_{22}$, also known as behenic acid), dotricontanoic acid ($C_{32}$), tetratriacontanoic acid ($C_{34}$), pentatriacontanoic acid ($C_{35}$), tetracontanoic acid ($C_{40}$), tetraacontanioc acid ($C_{44}$), dopentaacontanoic acid ($C_{54}$), tetrahexaacontanoic acid ($C_{64}$), and dohexaacontanoic acid ($C_{72}$). These monocarboxylic acids are available from many commercial suppliers, including Aldrich Chemical (Milwaukee, Wis.; www.sigma-aldrich.com).

Other suitable monocarboxylic acids are the oxidized (specifically, carboxyl terminated) polyethylene materials sold by Baker-Petrolite (Sugar Land, Tex.; www.bakerhughes.com/bapt/; division of Baker Hughes; www.bakerhughes.com) as their UNICID™ acids. UNICID™ acids are fully saturated, linear carboxylic acids with average carbon chain lengths ranging from $C_{24}$ to $C_{50}$. Acid values for UNICID™ acids vary from 60 to 115.

Still other suitable monocarboxylic acids are the alpha-branched carboxylic acids prepared by oxidizing higher molecular weight Guerbet alcohols. Such products are available from Jarchem Industries Inc. (Newark, N.J.; www-jarchem.com) as their JARIC™ acids. JARIC™ 1-36 acid is often a desirable monocarboxylic acid for the resins suitable to make the sunscreen composite particles of this invention.

The diamine reactant or compound has two amine groups, both of which are preferably primary amines, and is represented by the formula $HN(R^3)$—$R^4$—$N(R^3)H$. Each $R^3$ is preferably hydrogen, but may also be an alkyl group or may also join together with $R^4$ or another $R^3$ to form a heterocyclic structure. A preferred diamine is ethylene diamine, i.e., a diamine wherein $R^3$ is hydrogen and $R^4$ is —$CH_2CH_2$—.

Diamines other than ethylene diamine may be referred to herein as co-diamines. When present, co-diamines are preferably used in a minor amount compared to the ethylene diamine.

Exemplary co-diamines include 1,2-diaminopropane, 1,3-diaminopropane, 1,4-diaminobutane, 1,2-diamino-2-methylpropane, 1,3-diaminopentane, 1,5-diaminopentane, 2,3-dimethyl-1,3-propanediamine, 1,6-hexanediamine (also known as hexamethylenediamine, HMDA), 2-methyl-1,5-pentanediamine, 1,7-diaminoheptane, 1,8-diaminooctane, 2,5-dimethyl-2,5-hexandeiamine, 1,9-diaminononane, 1,10-diaminodecane, 1,12-diaminododecane, diaminophenanthrene (all isomers, including 9,10), 4,4'-methylenebis(cyclohexylamine), 2,7-diaminofluorene, phenylene diamine (1,3; 1,3 and/or 1,4 isomers), adamantane diamine, 2,4,6-trimethyl-1,3-phenylenediamine, 1,3-cyclohexanebis(methylamine), 1,8-diamino-p-menthane, 2,3,5,6-tetramethyl-1,4-phenylenediamine, diaminonaphthalene (all isomers, including 1,5; 1,8; and 2,3) and 4-amino-2,2,6,6-tetramethylpiperidine.

Suitable aromatic co-diamines (by which is meant molecules having two reactive, preferably primary amine groups (—$NH_2$) and at least one aromatic ring ("Ar") include xylene diamine and naphthalene diamine (all isomers).

Exemplary polyalkylene oxide-based co-diamines include without limitation, the JEFFAMINE™ diamines, i.e., poly (alkyleneoxy)diamines from Huntsman Chemical (Salt Lake City, Utah), also known as polyether diamines. Preferred polyalkylene oxide-containing co-diamines are the JEFFAMINE® ED, XTJ and D series diamines.

In certain embodiments, the polyamide resins suitable for use in this invention are prepared from co-diamine, where the co-diamine is selected from 1,6-hexanediamine, xylenediamine, 1,2-propanediamine, 2-methylpentamethylenediamine, and 1,12-dodecanediamine. Suitable diamines of the present invention are available from a number of commercial sources including Aldrich (Milwaukee, Wis.); EM Industries, Inc. (Hawthorne, N.Y.); Lancaster Synthesis, Inc. (Windham, N.H.) and Spectrum Quality Product, Inc. (New Brunswisk, N.J.).

The dibasic acid is an organic molecule containing two carboxylic acid groups or reactive equivalent thereof. A preferred dibasic acid is polymerized fatty acid, and in particular the dimer acid component of polymerized fatty acid. Polymerized fatty acid is typically a mixture of structures, including dimer acid and trimer acid, where individual dimer acids may be saturated, unsaturated, cyclic, acyclic, and combinations thereof. Polymerized fatty acid is typically formed by heating long-chain unsaturated fatty acids, e.g., $C_{18}$ monocarboxylic acids, to about 200-250° C. in the presence of a clay catalyst in order that the fatty acids polymerize. The product typically comprises dimer acid, i.e. $C_{36}$ dicarboxylic acid formed by dimerization of the fatty acid, and trimer acid, i.e., $C_{54}$ tricarboxylic acid formed by trimerization of the fatty acid. A more detailed discussion of fatty acid polymerization may be found in U.S. Pat. No. 3,157,681.

Because fatty acid polymerization typically forms much more dimer acid than trimer acid, those skilled in the art may often refer to polymerized fatty acid as dimer acid, even though some trimer acid, and even higher polymerization products, may be present with the dimer acid. It is preferred that the polymerized fatty acid contain less than about 20 weight percent of trimer acid, based on the total weight of the polymerized fatty acid, and that the dimer acid constitute at least about 80 weight percent of the polymerized fatty acid. More preferably, the dimer acid constitutes essentially all of the polymerized fatty acid.

Typical unsaturated fatty acids used to form polymerized fatty acid include oleic acid, linoleic acid and linolenic acid. Tall oil fatty acid, which is a mixture containing long-chain unsaturated fatty acids obtained as a byproduct of the wood pulping process, is preferred for preparing polymerized fatty acid.

Polymerized fatty acid may be hydrogenated prior to being used in the resin-forming reaction. Hydrogenation tends to provide for a slightly higher melting point and greater oxidative and color stability.

Polymerized fatty acid, dimer acid, and hydrogenated versions thereof may be obtained from a number of commercial suppliers. For example, Arizona Chemical (Jacksonville, Fla.) sells polymerized fatty acid under their UNDYME® trademark.

In addition to polymerized fatty acid, or reactive equivalents thereof, the dibasic acid may comprise a co-diacid. An exemplary co-diacid is a so-called "linear" diacid of the formula HOOC—$R^1$—COOH wherein $R^1$ is a linear $C_{4-17}$ hydrocarbon group, and more preferably is a linear $C_{6-8}$ hydrocarbon group. Linear co-diacids suitable for the present invention include 1,6-hexanedioic acid (adipic acid), 1,7-heptanedioic acid (pimelic acid), 1-8-octanedioic acid (suberic acid), 1,9-nonanedioic acid (azelaic acid), 1,10-decanedioic acid (sebacic acid), 1,11-undecanedioic acid, 1,12-dodecanedioic acid (1,10-decanedicarboxylic acid), 1,13-tridecanedioic acid (brassylic acid) and 1,14-tetradecanedioic acid (1,12-dodecanedicarboxylic acid).

Another exemplary co-diacid is the reaction product of acrylic or methacrylic acid (or the ester thereof, with a subsequent hydrolysis step to form an acid) and an unsaturated fatty acid. For example, a $C_{21}$ diacid of this type may be formed by reacting acrylic acid with a $C_{18}$ unsaturated fatty acid (e.g., oleic acid), where an ene-reaction presumably occurs between the reactants. An exemplary $C_2$, diacid is commercially available from Westvaco Corporation, Chemical Division, Charleston Heights, S.C. as their product number 1550.

Aromatic diacids may be used as the co-diacid. An "aromatic diacid" as used herein is a molecule having two carboxylic acid groups (—COOH) or reactive equivalents thereof (e.g., acid chloride (—COCl) or ester (—COOR) and at least one aromatic ring ("Ar"). Phthalic acids, e.g., isophthalic acid and terephthalic acid, are exemplary aromatic diacids.

In one aspect, the resin is prepared with co-diacid and the co-diacid is selected from 1,4-cyclohexane dicarboxylic acid, isophthalic acid, adipic acid, azelaic acid, sebacic acid, and dodecandoic acid.

A second class of polyamides useful for this invention are the ester-terminated poly(ester-amide) resins. These are prepared by reacting components comprising dibasic acid, diamine, polyol and monoalcohol, wherein at least 50 equivalent percent of the dibasic acid comprises polymerized fatty acid; and at least 50 equivalent percent of the diamine comprises ethylene diamine. Typical dibasic acids, and diamines have already been described hereinabove.

A further constituent of the ester-terminated poly(ester-amide) resins are the monoalcohol reactants. The monoalcohol may be represented by the formula $R^5$—OH, wherein $R^5$ is preferably a hydrocarbon group having at least ten carbon atoms. Thus, the monoalcohol can also be described as a monohydric alcohol. In one aspect, $R^5$ is a $C_{10-30}$-hydrocarbon, preferably a $C_{12-24}$ hydrocarbon, still more preferably is a $C_{16-22}$ hydrocarbon, and yet still more preferably is a $C_{18}$ hydrocarbon. Preferably, $R^5$ is linear, with the hydroxyl group located on a terminal carbon atoms, i.e., the monoalcohol is a primary monoalcohol. Thus, 1-dodecanol, 1-tetradecanol, 1-hexadecanol (cetyl alcohol), 1-octadecanol (stearyl alcohol), 1-eicosanol (arachidyl alcohol) and 1-docosanol (behenyl alcohol) are preferred monoalcohols for preparing polyamide resins of the invention.

Another suitable monoalcohol reactant is a so-called Guerbet alcohol. Guerbet alcohols have the general formula H—C(Ra)(Rb)-CH$_2$—OH wherein Ra and Rb may be the same or different and preferably represent a $C_{6-12}$ hydrocarbon group.

Another suitable monoalcohol reactant is a linear wax alcohol. Suitable linear wax alcohols are commercially available from, e.g., Petrolite Corporation (Tulsa, Okla.) under their UNILIN® trademark. These wax alcohols are typically a blend of linear alcohols having at least about 20 carbon atoms, and more typically at least about 24 carbon atoms.

A final ingredient employed when preparing ETPEA resin suitable for use in the present invention is polyol, which may also be referred to as polyhydric alcohol. The polyol is of the formula $R^6(OH)_t$ wherein $R^6$ is an n-valent organic group. For instance, $R^6$ may be a $C_2$-$C_{20}$ organic group without hydroxyl substitution. As another example, $R^6$ may be a hydrocarbon. Typically, t is an integer from about 2 to 6. Suitable polyols for use in preparing an ETPEA resin of the present invention include ethylene glycol, propylene glycol, butylene glycol, glycerol, trimethylolpropane, pentaerythritol, neopentyl glycol, tris(hydroxylmethyl)methanol, di-pentaerythritol, and tri-pentaerthyritol.

Preparation and description of the ETPEA resins are found in U.S. Pat. No. 7,329,719 B2 herein incorporated by reference.

UVA sunscreen can either be dispersed throughout the resin or can be formed as a core surrounded by resin. Dispersment throughout the resin is preferred. Typically, condensation polymerizable resin makes up from about 25 to about 98%, and preferably, from about 35 to about 85% by, and most preferably, from about 45 to about 75% by weight of the total weight of sunscreen composite particle, including all ranges subsumed therein where the particle is prepared with solvent comprising at least about 15% by weight UVA sunscreen dissolved therein. Amounts of UVA sunscreen (as added) that is often found in the sunscreen composite particles of this invention is typically from about 0.5 to about 55%, and preferably, from about 2 to about 50%, and most preferably, from about 3 to about 45% by weight, based on total weight of the particle and including all ranges subsumed therein.

Solvent suitable for use to make the sunscreen composite particle of this invention is limited only to the extent that the same is one in which the sunscreen is soluble in and that preferably has a dielectric constant from about 5.5 to about 9. In an especially preferred embodiment, the solvent allows for keto-enol tautomerization of the UVA sunscreen.

In a desired embodiment, the solvent is an imide, phthalimide based or a mixture thereof. In a more desired embodiment, the solvent comprises compounds represented by the formula:

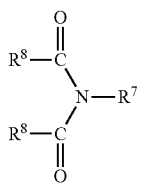

where $R^7$ is a $C_{1-8}$ linear or branched alkyl and each $R^8$ is independently H, OH, $C_{1-3}$ alkoxy or a $C_{1-5}$ alkyl group.

It is also with the scope of the invention to employ di- and/or tri-imides derived from the above-identified imide.

In a preferred embodiment, the solvent is a mixture of compounds represented by the formula:

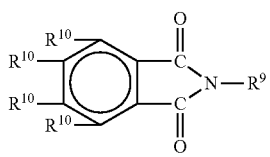

where $R^9$ is a $C_{1-6}$ linear or branched alkyl and each $R^{10}$ is independently H or a $C_{1-3}$ alkyl.

In a most preferred embodiment, $R^{10}$ is hydrogen and $R^9$ is a eutectic mixture comprising about 60 to about 70% by weight

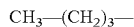

and about 25 to about 40% by weight

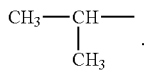

Such a mixture is referred to herein as butyl/isopropyl phthalimide.

When making particle, solvent typically makes up from about 10 to about 55%, and preferably, from about 12 to about 45%, and most preferably, from about 15 to about 35% by weight of the particle and including all ranges subsumed therein.

The size of the sunscreen composite particles (number average) of this invention may vary but typically the particles range from about 5 to about 3,000 nm, and preferably, from about 10 to 1500 nm, and most preferably, from about 40 to about 1200 nm, including all ranges subsumed therein.

When preparing compositions ready for use by consumers, such compositions typically comprise from about 0.1 to about 40%, and preferably, from about 0.5 to about 20%, and most preferably, from about 0.75 to about 12% by weight sunscreen composite particle, based on total weight of the composition and including all ranges subsumed therein.

Composite particles of this invention may be formulated into cosmetic compositions such as creams and lotions. These will feature generally preferred cosmetically acceptable carriers.

The carrier may be a liquid or solid material. Carriers may be present in amounts ranging from about 5 to about 98%, preferably from about 20 to about 95%, optimally from about 40 to about 80% by weight of the cosmetic compositions. Water is the most common carrier for this invention. Oily carriers in the presence of water and an emulsifier will form emulsion systems as carriers. These systems may either be water-in-oil or oil-in-water emulsions. Besides water, suitable carrier classes include silicones, polyhydric alcohols, fatty alcohols, hydrocarbons, triglycerides and thickening powders.

Concentrations of the fluid silicone may range from about 5% to about 60%, more preferably from about 5% to about 40%, by weight of the composition. These silicone fluids may be organic, silicone-containing or fluorine-containing, volatile or non-volatile, polar or non-polar.

Particularly preferred volatile silicone oils are cyclic volatile silicones wherein the repeating unit ranges from about 3 to about 5; and linear silicones wherein the repeating unit ranges from about 1 to about 7. Highly preferred examples of volatile silicone oils include cyclomethicones of varying viscosities, e.g., Dow Corning 200, Dow Corning 244, Dow Corning 245, and Dow Corning 344, and Dow Corning 345 (commercially available from Dow Corning Corp.) as well as SWS Silicones Corp (commercially available from SWS Silicones Corp.).

Hydrocarbons may be useful as cosmetically acceptable carriers for compositions of this invention. They may include mineral oil, petrolatum and polyalpha-olefins. Examples of preferred volatile hydrocarbons include polydecanes such as isododecane and isodecane (e.g., Permethyl-99A which is available from Presperse Inc.) and the $C_7$-$C_8$ through $C_{12}$-$C_{15}$ isoparaffins (such as the Isopar Series available from Exxon Chemicals).

Polyhydric alcohols may serve as carriers. Illustrative of this group are propylene glycol, dipropylene glycol, polypropylene glycol, polyethylene glycol, sorbitol, hydroxypropyl sorbitol, hexylene glycol, 1,3-butylene glycol, isoprene glycol, ethoxylated glycerol, propoxylated glycerol and mixtures thereof. Most preferred is glycerol known also as glycerin.

Fatty alcohols may also be useful carriers. The term "fatty" refers to carbon chain lengths ranging from 10 to 30 carbon atoms. Illustrative of this category are lauryl alcohol, cetyl alcohol, stearyl alcohol, isostearyl alcohol and combinations thereof.

Triglycerides are another group of materials useful as carriers. Illustrative but not limiting are sunflower seed oil, cotton oil, canola oil, soybean oil, castor oil, borage oil, olive oil, shea butter, jojoba oil and mixtures thereof. Mono- and di- glycerides may also be useful. Illustrative of these categories are glyceryl monostearate and glyceryl distearate. Often preferred are the triglycerides referred to as caprylic/capric triglycerides.

The carriers can comprise one or more thickening agents, preferably from about 0.05% to about 10%, more preferably from about 0.1% to about 5%, and even more preferably from about 0.25% to about 4%, by weight for the composition. Nonlimiting classes of thickening agents include those selected from the group consisting of:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the Carbomers, which are homopolymers of acrylic acid crosslinked with allyl ethers of sucrose or pentaerytritol. The Carbomers are available as the Carbopol® 900 series from Noveon Corporation (e.g. Carbopol® 954). In addition, other suitable carboxylic acid polymeric agents include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as Acrylates/$C_{10-30}$ Alkyl Acrylate Crosspolymers and are commercially available as Carbopol® 1342, Carbopol® 1382, Ultrez® 21, Pemulen® TR-1, and Pemulen® TR-2, from Noveon Corporation.

b. Taurate Polymers

The compositions of the present invention can optionally comprise crosslinked taurate polymers useful as thickeners or gelling agents including anionic, cationic and nonionic polymers. Examples include Hydroxyethyl Acrylate/Sodium Acryloyldimethyl Taurate (e.g. Simulgel® NS and INS 100), Acrylate/Sodium Acryloyldimethyl Taurate (e.g. Simulgel® EG), Sodium Acryloyldimethyl Taurate (e.g. Simulgel® 800) and Ammonium Acryloyldimethyl Taurate/Vinyl Pyrrolidone (e.g. Aristoflex® AVC).

c. Polyacrylamide Polymers

The compositions of the present invention can optionally comprise vinyl polymerized polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the tradename Sepigel® 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

d. Polysaccharides

A wide variety of polysaccharides are useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof.

e. Gums and Clays

Other thickening and gelling agents useful herein include materials that are primarily derived from natural sources. Nonlimiting examples include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, laponite, bentonite, hyaluronic acid, hydrated silica, hydroxypropyl chitosan, hydroxypropyl guar, karaya gum, kelp, locust bean gum, natto gum, potassium carrageenan, propylene glycol alginate, sclerotium gum, sodium carboxymethyl dextran, sodium carrageenan, tragacanth gum, xanthan gum, and mixtures thereof.

The compositions of the present invention may contain one or more other particulate materials. Nonlimiting examples of other particulate materials include colored and uncolored pigments, interference pigments, inorganic powders, organic powders, composite powders, optical brightener particles, and combinations thereof. Particulate materials may be present from about 0.01% to about 20%, more preferably from about 0.05% to about 10%, still more preferably from about 0.1% to about 5%, by weight of the composition.

Other particulate materials useful herein include but are not limited to bismuth oxychloride, sericite, mica, mica treated with barium sulfate or titanium dioxide, zeolite, kaolin, silica, boron nitride, lauroyl lysine, nylon, talc, styrene, polystyrene, ethylene/acrylic acid copolymer, aluminum oxide, barium sulfate,) calcium carbonate, cellulose acetate, PTFE, polymethyl methacrylate, starch, modified starches, silk, glass, and mixtures thereof. Preferred organic powders/fillers include polymeric particles chosen from the methylsilsesquioxane resin microspheres such as those sold by Toshiba Silicone under the name Tospearl 145A; microspheres of polymethylmethacrylates such as those sold by Seppic under the name Micropearl M 100; the spherical particles of crosslinked polydimethylsiloxanes, especially such as those sold by Dow Corning Toray Silicone under the name Trefil E 506C or Trefil E 505C; spherical particles of polyamide and more specifically Nylon 12, especially such as those sold by Atochem under the name Orgasol 2002N Nat C05; polystyrene microspheres such as those sold by Dyno Particles under the name Dynospheres; ethylene acrylate copolymer sold by Kobo under the name FloBead EA209; PTFE; polypropylene; aluminum starch octenylsuccinate such as sold by National Starch under the name Dry Flo; microspheres of polyethylene such as those sold by Equistar under the name of Microthene FN510-00; silicone resin; platelet shaped powder made from L-lauroyl lysine, and mixtures thereof. Especially preferred are spherical powders with an average primary particle size from 0.1 to 75 microns, preferably from 0.2 to 30 microns.

The compositions (i.e., not the sunscreen composite particle) may optionally have additional sunscreen added thereto. Illustrative examples include benzophenones, UV grade zinc oxide, as well as octyl methoxycinnamate, phenylbenzimidazole, methyl anthranilate, homosalate, octisalate, octocrylene, octyldimethyl PABA, ortho-aminobenzoates, UVA grade $TiO_2$, mixtures thereof or the like. Such sunscreens when added typically make up less than 30% by weight of the composition and often from about 0.01 to about 15% by weight of the composition, including all ranges subsumed therein.

Cosmetic compositions formulated with sunscreen composite particles of the present invention may also contain components to enhance physical properties and performance.

Such components, when incorporated into the cosmetic compositions, should be suitable for use in contact with human keratinous tissue without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these classes include: abrasives, absorbents, aesthetic components such as fragrances, pigments, colorings/colorants, essential oils, emulsifiers (like cetearyl alcohol and Cetearth sold as Promulgen D, PEG-100 stearate, Cholesterol NF, soap, alkyl ether sulfates, alkyl sulfonates, distearyl dimonium chloride, $C_{12-20}$ trialkyl betaines and mixtures thereof), skin sensates, astringents, etc. (e.g. clove oil, menthol, camphor, eucalyptus oil, eugenol, menthyl lactate, witch hazel distillate), anti-acne agents, anti-caking agents, antifoaming agents, antimicrobial agents, antioxidants, biological additives, buffering agents, bulking agents, chelating agents, chemical additives (like disodium EDTA), colorants, cosmetic astringents, cosmetic biocides, denaturants, drug astringents, external analgesics, film forming polymers (like isohexadecane), opacifying agents (like $TiO_2$), pH adjusters, propellants, reducing agents, sequestrants, skin bleaching and lightening agents, skin conditioning agents, skin soothing and/or healing agents and derivatives, skin treating agents, thickeners (such as fatty acids having from 10 to 30 carbon atoms like stearic, isostearic, hydroxystearic and ricinoleic acid), and vitamins and derivatives thereof.

A safe and effective amount of an anti-oxidant/radical scavenger may be added in amounts from about 0.01% to about 10%, more preferably from about 0.1% to about 5% by weight of the composition.

Anti-oxidants/radical scavengers may be employed such as ascorbic acid (vitamin C) and its salts, ascorbyl esters of fatty acids, ascorbic acid derivatives (e.g. magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolor®), amines (e.g. N,N-diethylhydroxylamine, amino-guanidine), nordihydroguaiaretic acid, bioflavonoids, amino acids, silymarin, tea extracts, and grape skin/seed extracts. Preferred anti-oxidants/radical scavengers are selected from esters of tocopherol, more preferably tocopherol acetate.

The compositions comprising the sunscreen composite particles of this invention may, if desired, comprise a flavonoid compound. Flavonoids are disclosed in U.S. Pat. Nos. 5,686,082 and 5,686,367 herein incorporated by reference. Examples of flavonoids particularly suitable flavones, isoflavones, coumarins, chromones, discoumarols, chromanones, chromanols, isomers (e.g. cis/trans isomers) thereof, and mixtures thereof.

Preferred for use are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy), and mixtures thereof. Flavonoid compounds useful herein are commercially available from a number of sources, e.g., Indofine Chemical Company, Inc., Stearloids, Inc., and Aldrich Chemical Company, Inc. The herein described flavonoid compounds are preferably present in from about 0.01% to about 20%, more preferably from about 0.1% to about 10%, and even more preferably from about 0.5% to about 5% by weight.

Anti-inflammatory agents useful herein include allantoin and compounds of the Licorice (the plant genus/species *Glycyrrhiza glabra*) family, including glycyrrhetic acid, glycyrrhizic acid, and derivatives thereof (e.g. salts and esters).

The compositions may comprise a tanning active. When present, it is preferable that the compositions comprise from about 0.1% to about 20%, more preferably from about 2% to about 7% by weight tanning active based in total weight of the composition. A preferred tanning active is dihydroxyacetone.

The compositions may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include niacinamide, kojic acid, arbutin, tranexamic acid, placental extract, ascorbic acid and derivatives thereof (e.g. magnesium ascorbyl phosphate, sodium ascorbyl phosphate, ascorbyl glucoside, and ascorbyl tetraisopalmitates). Other skin lightening materials suitable for use herein include Actiwhite® (Cognis), Emblica® (Rona), Azeloglicina (Sinerga) and extracts (e.g. mulberry extract).

The compositions of this invention may comprise an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and even more preferably from about 0.05% to about 2% by weight of the composition.

Preservatives can desirably be incorporated into the compositions with the comprising sunscreen composite particles of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate (including mixtures with DMDH hydantoin sold under the name Glydant Plus®), phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition, including all ranges subsumed therein. Such preservatives may be added to the composition directly or to the sunscreen composite particle during the manufacturing of the same.

Preferred examples of these actives include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cystein, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, climbazole, miconazole, ketoconazole, neocycin sulfate, and mixtures thereof.

The compositions of this invention may comprise a conditioning agent selected from the group consisting of humectants, moisturizers, or skin conditioners. A variety of these materials can be employed and each can be) present at a level of from about 0.01% to about 40%, more preferably from about 0.1% to about 30%, and even more preferably from about 0.5% to about 15% by weight of the composition. These materials include, but are not limited to, guanidine; urea; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy compounds such as sorbitol, mannitol, glycerol, hexanetriol, butanetriol, propylene glycol, butylene glycol and hexylene glycol; polyethylene glycols; sugars and starch derivatives (e.g. alkoxylated glucose, fructose, sucrose, trehalose); hyaluronic acid; lactamide monoethanolamine; acetamide monoethanolamine; sucrose polyester; petrolatum; and mixtures thereof.

The sunscreen composite particles and compositions are generally made by mixing the desired ingredients under moderate shear and atmospheric pressure. Heating is often desired whereby temperatures preferably do not exceed 120° C.

The compositions of this invention include but are not limited to lotions, milks, mousses, serums, sprays, aerosols, foams, sticks, pencils, gels, creams and ointments. The compositions may also be applied via a woven or nonwoven synthetic and/or natural fibered textile (wipe or towelette).

The examples below are provided to further illustrate an understanding of the claimed invention. The examples are not intended to limit the scope of the claims.

EXAMPLE 1

A typical process to manufacture the sunscreen composite particles of this present invention is herein described. Water, in the amount of 300 grams was charged to a vessel fitted with an Escolabor™ mixer (1 liter model manufactured in Riehn, Switzerland) which has scrape surface blades (Scraper). The water was then heated to 60° C. A metal beaker was charged with 50 grams of resin like Sylvaclear AF1900V®, 20 grams of UVA sunscreen such as 4-(1,1-dimethylethyl)-4"-methoxydibenzoylmethane (Avobenzone) and 30 grams of solvent i.e., butyl/isopropyl phthalimide (dielectric constant 7.0). The beaker was placed in a water bath. The resin mixture was heated up to about 90-105° C. and mixed until homogenous. The resin from the beaker was then added slowly to the vessel of heated water with slow mixing (20% power use on the scraper) followed by a cooling period. Composite particles of the present invention were then separated (via centrifuge) as particulates from the aqueous phase. The particulates were found to have a pH of about 5.8, a dielectric constant of 7.4, and a diameter (number average particle size) of circa 280 nm.

EXAMPLE 2

The composite particles of this Example were made in a manner similar to the one used to make the particles of Example 1 except that 50 grams of Sylvaclear® PA1200V resin were used in lieu of 50 grams of Sylvacare® AF1900V resin, 35 grams of dibutyl adipate (dielectric constant 4.2) were used as solvent in lieu of 30 grams of butyl/isopropyl phthalimide, and 15 grams of Avobenzone were used in lied of 20 grams.

EXAMPLE 3

A series of comparative compositions/samples were prepared with sunscreen composite particles to demonstrate the unexpected aspects of the present invention. The results obtained are a direct result of the assessments made with the compositions identified below.

The compositions were prepared by combining the phases in the Table I below. Phases A and B were combined with mixing and with heating to a temperature of about 80 to 85° C. Phases C to H were added with moderate stirring whereby the temperature of the resulting mixture was maintained at about 55 to 60° C. The mixture made was homogenized and Phase I was added thereto during homogenization and at a temperature of about 45° C. Complete mixing was achieved within 5 to 10 minutes. Phase J was added with temperature maintained at about 40° C. Conditions were atmospheric and water made up the balance of the compositions.

TABLE I

| | \multicolumn{11}{c}{Compositions/Samples} |
| Ingredient | 1 % w/w | 2 % w/w | 3 % w/w | 4 % w/w | 5 % w/w | 6 % w/w | 7 % w/w | 8 % w/w | 9 % w/w | 10 % w/w | 11 % w/w |
| --- | --- | --- | --- | --- | --- | --- | --- | --- | --- | --- | --- |
| PHASE A | | | | | | | | | | | |
| Water deionized | Balance | Balance | Balance | Balance | Balance | Balance | Balance | Balance | Balance | Balance | Balance |
| Disodium EDTA | 0.10 | 0.10 | 0.10 | 0.10 | 0.10 | 0.10 | 0.10 | 0.10 | 0.10 | 0.10 | 0.10 |
| Glycerin | 5.00 | 5.00 | 5.00 | 5.00 | 5.00 | 5.00 | 5.00 | 5.00 | 5.00 | 5.00 | 5.00 |
| Preservative | 0.10 | 0.10 | 0.10 | 0.10 | 0.10 | 0.10 | 0.10 | 0.10 | 0.10 | 0.10 | 0.10 |
| PHASE B | | | | | | | | | | | |
| Nonionic emulsifier | 2.77 | 2.77 | 2.77 | 2.77 | 2.77 | 2.77 | 2.77 | 2.77 | 2.77 | 2.77 | 2.77 |
| PEG-100 Stearate | 1.65 | 1.65 | 1.65 | 1.65 | 1.65 | 1.65 | 1.65 | 1.65 | 1.65 | 1.65 | 1.65 |
| Avobenzone | 1.00 | 1.00 | — | — | — | — | — | — | — | — | — |
| Caprylic/Capric Triglyceride | 8.75 | 8.75 | 8.75 | 8.75 | 8.75 | 8.75 | 8.75 | 8.75 | 8.75 | 8.75 | 8.75 |
| Stearic Acid | 0.46 | 0.46 | 0.46 | 0.46 | 0.46 | 0.46 | 0.46 | 0.46 | 0.46 | 0.46 | 0.46 |
| Preservative | 0.20 | 0.20 | 0.20 | 0.20 | 0.20 | 0.20 | 0.20 | 0.20 | 0.20 | 0.20 | 0.20 |
| Cholesterol NF | 0.92 | 0.92 | 0.92 | 0.92 | 0.92 | 0.92 | 0.92 | 0.92 | 0.92 | 0.92 | 0.92 |
| PHASE C | | | | | | | | | | | |
| TiO2 | 2.00 | — | 2.00 | 2.00 | — | — | — | — | — | — | — |
| PHASE D | | | | | | | | | | | |
| Isohexadecane | 0.50 | 0.50 | 0.50 | 0.50 | 0.50 | 0.50 | 0.50 | 0.50 | 0.50 | 0.50 | 0.50 |
| DC 200 Dimethicone | 0.25 | 0.25 | 0.25 | 0.25 | 0.25 | 0.25 | 0.25 | 0.25 | 0.25 | 0.25 | 0.25 |
| PHASE G | | | | | | | | | | | |
| Aristoflex AVC | 1.0 | 1.0 | 1.0 | 1.0 | 1.0 | 1.0 | 1.0 | 1.0 | 1.0 | 1.0 | 1.0 |
| PHASE H | | | | | | | | | | | |
| DC 245 Dimethicone | 8.50 | 8.50 | 8.50 | 8.50 | 8.50 | 8.50 | 8.50 | 8.50 | 8.50 | 8.50 | 8.50 |
| PHASE I | | | | | | | | | | | |
| Sunscreen composite particle Example 1 | | | | | 5.00 | | 5.00 | | | | |
| Sunscreen composite particle Example 2 | | | 6.67 | | | 6.67 | | | | | |
| Polymer composite butyl/isopropyl phthalimide* | | | | | | | | | 5.00 | | 5.00 |
| Polymer composite dibutyl adipate** | | | | | | | | 6.67 | | 6.67 | |

TABLE I-continued

| Ingredient | Compositions/Samples | | | | | | | | | | |
|---|---|---|---|---|---|---|---|---|---|---|---|
| | 1 % w/w | 2 % w/w | 3 % w/w | 4 % w/w | 5 % w/w | 6 % w/w | 7 % w/w | 8 % w/w | 9 % w/w | 10 % w/w | 11 % w/w |
| PHASE J | | | | | | | | | | | |
| Phenoxyethanol | 0.20 | 0.20 | 0.20 | 0.20 | 0.20 | 0.20 | 0.20 | 0.20 | 0.20 | 0.20 | 0.20 |
| Water deionized | 1.00 | 1.00 | 1.00 | 1.00 | 1.00 | 1.00 | 1.00 | 1.00 | 1.00 | 1.00 | 1.00 |
| TOTAL | 100.00 | 100.00 | 100.00 | 100.00 | 100.00 | 100.00 | 100.00 | 100.00 | 100.00 | 100.00 | 100.00 |

*Same particle of Example 1, except no sunscreen was used, 50% by weight resin and solvent.
**Same particle of Example 2, except no sunscreen was used, 50% by weight resin and solvent.

SPF Measurements

Sun protection factor (SPF) was measured in vitro using an Optometrics SPF 290 instrument. The test procedure required calibration of the monochrometer and sample stage of the Optometrics SPF 290 instrument. Thereafter the instrument was calibrated with a blank sample quartz plate (10 cm×10 cm and 3 mm thickness). Calibration zeros the UV detector. Compositions were applied and spread uniformly onto plates to leave a film of 2 mg/cm$^2$. The films were left to dry for 30 minutes. Subsequently, SPF and Spectral intensify readings were taken on the dried films using twelve measurements on different parts of the coated quartz plates and recording average values.

Results of the SPF testing and each of the compositions are summarized below. Assessed were the average SPF value and absorbtion intensities in monochromatic protection factor units and at wavelengths of 360 nm (UVA region) and 290 nm (UVB region).

Results

Compositions 1, 3 and 4, subsequent to assessment, unexpectedly reveal that composition made consistent with this invention and having sunscreen composite particles as defined herein have a higher (about three times) UVA absorbtion (at 360 nm) than sunscreen in oil (composition 1) and about 25% higher (at 360 nm) when compared to particle made with dibutyl adipate (composition 2). For UVB absorbtion (at 290 nm), compositions 1 and 3 had similar UVB absorbtion, attributable to the use of TiO$_2$. Composition 4, on the otherhand, unexpectedly had about twice the UVB absorbtion when compared to compositions 1 and 3. The results surprisingly show that composition made consistent with this invention display excellent UVB absorbtion characteristics in the absence of a supplied UVB sunscreen.

Compositions 2, 5 and 6 show that composited sunscreen (composition 5) displays better (about 2.5 times) UVA absorption (at 360 nm) than sunscreen in oil (composition 2). The results surprisingly show that a composition made consistent with this invention (composition 6) displays about 25% higher UVA absorption when compared to composition 5 having composited sunscreen not made consistent with this invention. For UVB absorption (290 nm), composition 6 unexpectedly showed at least 10 times more UVB absorbtion than compositions 2 and 5 where no contribution to TiO$_2$ is made since the compositions are deplete of the opacifier.

Compositions 7, 8 and 9 were assessed, the compositions being deplete of TiO$_2$ opacifier and sunscreen. The compositions displayed no UVA or UVB absorption, surprisingly indicating that the solvent/polymer composite system has essentially no effect on absorption in the absence of a sunscreen suitable to undergo keto-enol tautomerization.

Compositions 10 and 11 display no UVB absorbtion, demonstrating that sunscreen suitable to undergo keto-enol tautomerization in solvent does not yield UVB absorbtion if physically outside of the sunscreen composite particle described in this invention.)

TABLE 2

| Composition | Sample | | |
|---|---|---|---|
| | UVA absorption | UVB absorption | SPF value |
| 1 | 26.1 | 24.8 | 13.4 |
| 2 | 16.2 | 2 | 3.9 |
| 3 | 63.4 | 25.7 | 23.2 |
| 4 | 80.5 | 50.2 | 33.4 |
| 5 | 52.1 | 1.8 | 10.2 |
| 6 | 65.1 | 21.0 | 21.1 |
| 7 | 1.0 | 0.96 | 1.0 |
| 8 | 1.0 | 1.4 | 1.0 |
| 9 | 1.0 | 0.95 | 1.0 |
| 10 | 17.1 | 1.3 | 4.1 |
| 11 | 16.4 | 1.6 | 3.8 |

The results unexpectedly confirm excellent UVA and UVB protection when making compositions consistent with this invention.

What is claimed is:

1. A composition for providing UVA and UVB protection, the composition comprising a cosmetically acceptable carrier, and a sunscreen composite particle comprising:
   a) an UVA sunscreen that can undergo keto-enol tautomerization, wherein said UVA sunscreen is 4-(1,1-dimethylethyl)-4'-methoxydibenzoylmethane;
   b) a condensation polymerizable resin selected from the group consisting of polyalkyleneoxypolyamide (PAOPA) resins wherein said polyalkyleneoxypolyamide resin is polyamide-3; and
   c) a solvent, the solvent being one in which the UVA sunscreen is soluble in and one having a dielectric constant from about 5.5 to about 9, wherein said solvent is butyl/isopropyl phthalimide,
   wherein the particle imparts UVA and UVB sunscreen protection and is substantially free of added UVB sunscreen.

2. The composition according to claim 1 wherein the UVA sunscreen can dissolve in the solvent to yield a solution which is at least 15% by UVA sunscreen based on total weight of sunscreen and solvent.

3. A method for obtaining UVA and UVB protection comprising the step of topically applying to skin the composition of claim 1.

* * * * *